(12) United States Patent
Healy et al.

(10) Patent No.: US 6,364,894 B1
(45) Date of Patent: Apr. 2, 2002

(54) METHOD OF MAKING AN ANGIOPLASTY BALLOON CATHETER

(75) Inventors: Stephen R. Healy, Miami; Jason White, Miami Lakes, both of FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/592,499

(22) Filed: Jun. 12, 2000

(51) Int. Cl.[7] .............................................. A61M 29/02
(52) U.S. Cl. ...................................................... 606/194
(58) Field of Search .............................. 604/96.01, 280, 604/282, 273, 97.01, 98.01, 99.01, 103, 103.1, 529; 606/194, 191, 192

(56) References Cited

U.S. PATENT DOCUMENTS

| | | | |
|---|---|---|---|
| 5,156,612 A | * 10/1992 | Pinchuk et al. | 606/194 |
| 5,304,134 A | * 4/1994 | Kraus et al. | 604/96 |
| 5,567,203 A | * 10/1996 | Euteneuer et al. | 604/96 |
| 5,643,209 A | * 7/1997 | Fugoso et al. | 604/96 |
| 5,649,909 A | * 7/1997 | Cornelius | 604/96 |
| 5,653,691 A | * 8/1997 | Rupp et al. | 604/96 |
| 5,769,819 A | * 6/1998 | Schwab et al. | 604/103 |
| 5,891,110 A | 4/1999 | Larson et al. | |
| 6,048,338 A | 4/2000 | Larson et al. | |

* cited by examiner

Primary Examiner—Eduardo C. Robert
(74) Attorney, Agent, or Firm—Michael W. Montgomery

(57) ABSTRACT

A balloon catheter for medical treatment of a patient has a proximal hub, flexible catheter shaft, a balloon, and an improved tip design. The catheter defines a guidewire lumen defined by a tubular inner body extending from a distal guidewire port to a proximal port located at a position proximal from the balloon. The guidewire lumen preferably has a constant cross-sectional area from the distal guidewire port to the proximal end of the balloon. At least one marker band is affixed to the inner body at a location within the balloon. A distal leg of the balloon is affixed to the inner body and a location between the marker band and the distal end of the inner body. A portion of the inner body extending in the proximal direction from the marker band has a substantially constant inner lumen diameter. However, the inner body wall thickness tapers to a narrower tip wall thickness, extending from a location between the marker band and the balloon distal leg, to the distal end of the inner body. A distal portion of the distal leg is also preferably tapered.

4 Claims, 2 Drawing Sheets

METHOD OF MAKING AN ANGIOPLASTY BALLOON CATHETER

BACKGROUND AND SUMMARY OF THE INVENTION

1. Technical Background

The present invention relates generally to medical devices, and more particularly to a balloon catheter having an improved tip design.

2. Discussion

Balloon catheters are used in a variety of therapeutic applications, including many vascular treatments such as angioplasty. Angioplasty can be used to treat vascular disease, in which blood vessels may be partially or totally blocked or narrowed by a lesion or stenosis. In many instances of vascular disease, a local area of a blood vessel may become narrowed. This narrowing is called a lesion or stenosis, and may take to form of hard plaque, cholesterol, fats, or viscous thrombus. Such a stenosis may cause heart attack or stroke, which are significant health problems affecting millions of people each year.

During angioplasty, an expansive force may be applied to the lumen of the stenosis, which may be a vessel constriction due to plaque buildup or thrombus, etc. This outward pressing of a constriction or narrowing at the desired site in a body passage is intended to partially or completely reopened or dilate that body passageway or lumen, increasing its inner diameter or cross-sectional area. The objective of this procedure is to increase the inner diameter or cross-sectional area of the vessel passage or lumen through which blood flows, to encourage greater blood flow through the newly expanded vessel.

As an example, the present invention will be described in relation to coronary, peripheral, and neuromuscular angioplasty. However, it should be understood that the present invention relates to any angioplasty catheter having the features of the present invention, and is not limited to catheters for a particular therapeutic procedure.

Some balloon catheters have a relatively long and flexible tubular shaft defining one or more passages or lumens, extending between a hub at a proximal end to a distal end where the balloon is located. The catheter shaft may define an inflation lumen for conducting inflation fluid from an inflation port defined by the proximal hub to selectively inflate or deflate the balloon, and may define a guidewire lumen extending from a distal guidewire port at the distal end of the catheter to a proximal port located at a position proximal from the balloon.

The guidewire lumen may be defined by a tubular inner body extending from a distal end of the catheter proximally through the entire length of the balloon. Whatever structural element defines the guidewire lumen, the inner diameter or cross-sectional area of the guidewire lumen is preferably large enough to accommodate the size of the desired guidewire. Likewise, the inner diameter of the guidewire lumen in the region of the balloon may preferably be constant, to facilitate easy movement of the guidewire within the guidewire lumen.

One possible shaft design is a coaxial arrangement of tubular inner and outer bodies, with a distal balloon leg affixed to the inner body, and a proximal balloon affixed to a distal end of the outer body.

During a common treatment method for using such a balloon catheter, a physician advances the catheter into the body of the patient, by directing the catheter distal end percutaneously through an incision and along a body passage, until the balloon is located within the desired site. The term "desired site" refers to the location in the patient's body currently selected for treatment by a physician.

As the balloon catheter is advanced along the desired vascular path, the performance of the catheter design may be evaluated by analyzing various characteristics, including column strength, pull strength, flexibility, push ability, traceability, and cross ability. The term "cross ability" usually refers to the ability to the catheter to successfully transmit pushing and guiding and steering forces applied at the proximal hub by the physician, such that the distal tip of the balloon catheter pushes into, through and past a constricted lesion. In addition, the desired performance of the balloon catheter enables it to follow a tortuous vascular path without injuring the vessel, prolapsing the guidewire or kinking. The term "traceability" refers to the combination of characteristics that allows a catheter to follow the desired path.

As an example of prior balloon catheters, U.S. Pat. No. 5,891,110 entitled "Over-The-Wire Catheter With Improved Traceability," issued to Lagoon et al. on Apr. 6, 1999 shows a balloon catheter having an inner tube with outer and inner walls that distally taper from larger diameters to smaller diameters, as well as an area adjacent to the balloon distal seal that is backfilled with adhesive to provide a smooth transition.

However, the present invention is improved over prior catheters, and relates to an improved tip design for a balloon catheter. One of the possible components of the present balloon catheter is a tubular inner body drawn down to reduce the outer dimension, but substantially maintain the inner lumen dimensions. This wall thickness optimization located inside the balloon preferably cooperates with a shaved and tapered distal leg of the balloon which is sealed to the inner tubular body forming a smooth and gentle leading-edge taper.

The catheter tip design should also preferably provide all of the desired performance characteristics, including flexibility with column strength. The present improved tip design may include the following novel features in combination: substantially constant guidewire lumen diameter, tubular inner and outer bodies, a wall thickness draw down of the inner body located between a marker band and the balloon distal leg seal, and a leading-edge taper of the distal balloon leg which is formed by shaving the balloon leg. The inner body distal end may also have a tip buff or end manicure to provide a gentle distal tip and to closely surround the guidewire.

These and various other objects, advantages and features of the invention will become apparent from the following description and claims, when considered in conjunction with the appended drawings.

DETAILED DESCRIPTION OF THE PREFERRED EMBODIMENT

Figure 1:
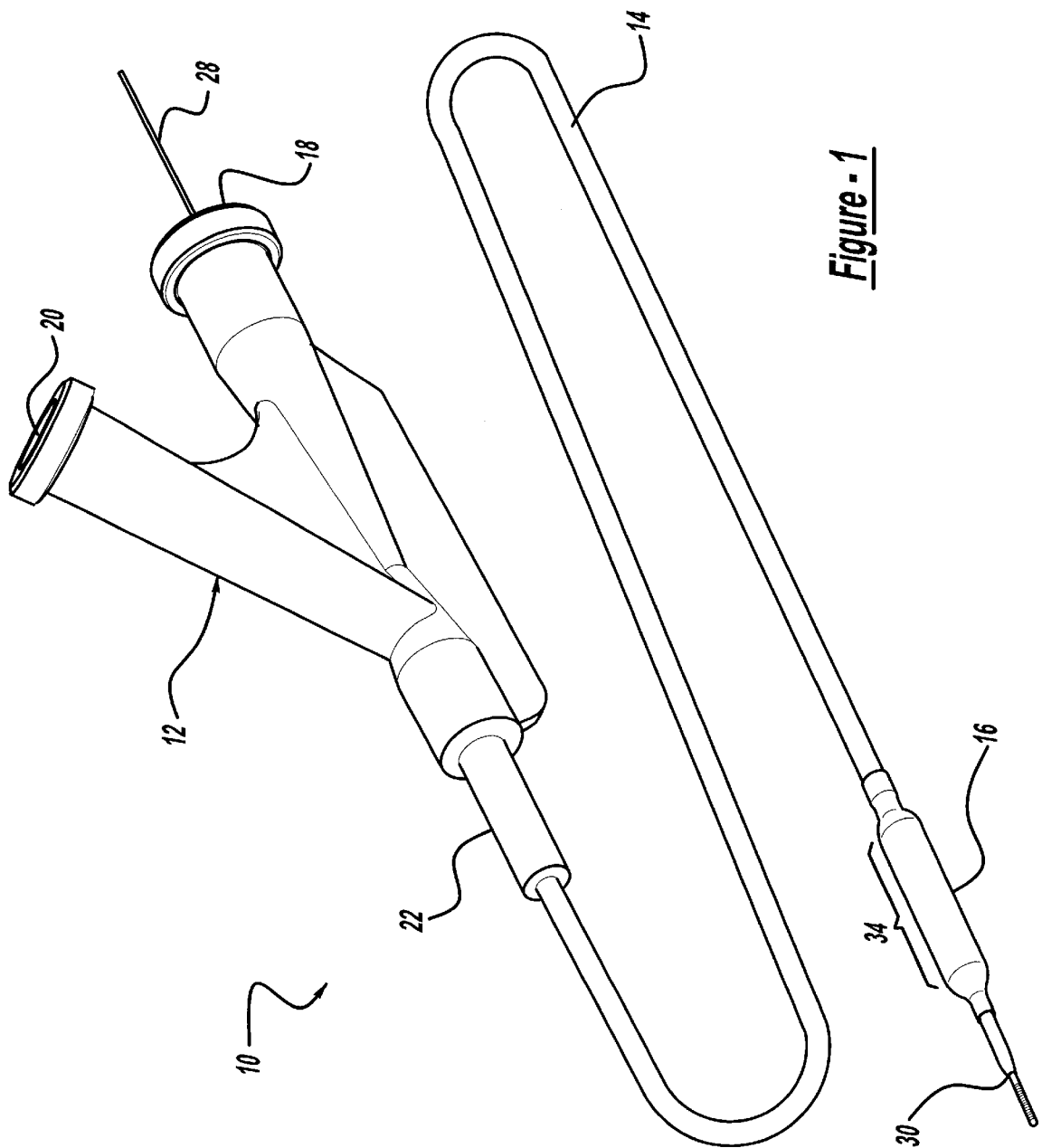
FIG. 1 is a partial longitudinal cross-section view of a balloon catheter, arranged according to the principles of the present invention.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a balloon catheter is depicted, with one of the preferred embodiments of the present invention being shown generally at 10. The illustrated balloon catheter of course illustrates only one of many different balloon catheter designs within the scope of the present invention.

The illustrated embodiment shows the improved tip design of the present invention, and includes a proximal hub 12, a flexible catheter shaft 14, and a balloon 16. The proximal hub 12 preferably provides an operating handle for a physician, as well as a proximal guidewire port 18 and an inflation port 20. A tubular strain relief 22 bridges the transition between the proximal hub 12 and the flexible shaft 14.

Figure 2:
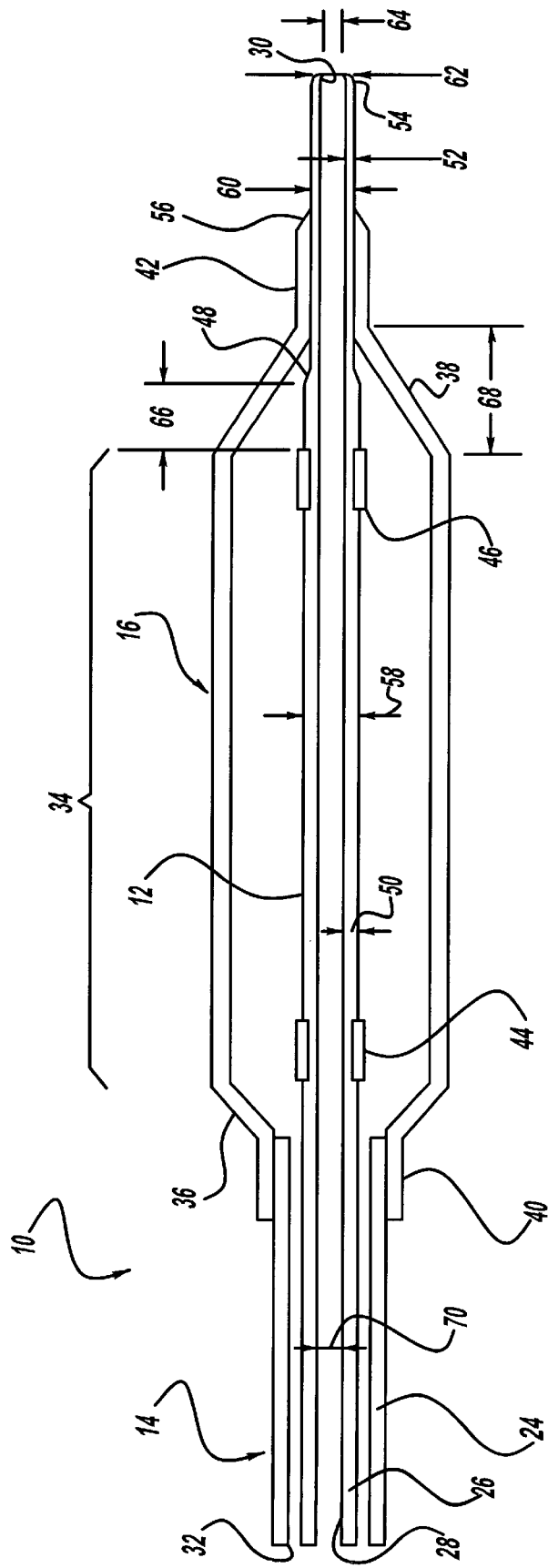
FIG. 2 is an external diagrammatic view of a balloon catheter, arranged according to the principles of the present invention.

The distal portion of the balloon catheter 10 is shown in more detail in FIG. 2. At least a distal portion of the catheter shaft 14 has the coaxial arrangement as shown in FIG. 1, including a tubular outer body 24 surrounding a portion of a tubular inner body 26. The inner body 26 defines a guidewire lumen 28 having a lumen diameter 70, extending from a distal guidewire port 30 defined at the distal tip of the inner body 26 to the proximal guidewire port 18. Guidewire lumen 28 can slidingly accept a guidewire 72. An inflation lumen 32 is defined by the annular space between the outer body 24 and inner body 26, extending from the proximal inflation port 20 to the balloon interior.

The balloon 16 preferably has a central cylindrical working portion 34, proximal and distal tapering portions 36 and 38, and proximal and distal legs 40 and 42. The balloon proximal leg 40 is affixed to a distal end of the outer body 24 by any suitable method, including heat-sealing or adhesives. Likewise, the balloon distal leg 42 is affixed to the inner body 26 near its distal end by any suitable method. The positions of the proximal and distal ends of the balloon cylindrical working portion 34 may be indicated under fluoropropyl by a pair of proximal and distal radiopaque marker bands 44 and 46 affixed to the inner body 26.

The present invention provides a novel improved tip design having an optimized bundle of performance characteristics, including pull strength, column strength, a relatively smooth flexibility curve along the length of the catheter, and distal tip flexibility, minimum deflated outer profile, maximum guidewire lumen inner diameter, and hoop strength of the tubular inner body, and maximum flexibility at the distal tip.

Accordingly, the illustrated preferred embodiment of the present balloon catheter preferably has a draw down wall thickness transition 48 of the tubular inner body 26 located between the distal marker band 46 and the balloon distal leg 42, resulting in the tubular inner body 26 having a composite wall thickness. The inner body 26 thus has a first wall thickness 50 and a first outer diameter 58 extending from the transition 48 in a proximal direction through the length of the balloon 16, and a second smaller wall thickness 52 and a second outer diameter 60 extending from the transition 48 in a distal direction substantially to the distal tip of catheter 10.

Also, the extreme distal end of the catheter may preferably have a tip buff 54, in which the tubular inner body 26 is manicured to smooth any possible rough edges.

This smaller distal wall thickness 52 of the inner body 26 provides a smaller distal profile which assists in crossing tight lesions, and enhances the flexibility of the entire distal tip of the catheter 10. In addition, the inner body guidewire lumen 28 diameter is maintained throughout the length of the catheter 10, except for the tip buff 54 at the extreme distal end of the catheter 10, which maximizes the size of the guidewire that the catheter 10 can accept through the guidewire lumen 28.

The first wall thickness 50 portion of the inner body 26 provides the desired features of enhanced pull strength, column strength, hoop strength, and structural support for the marker bands. Also, locating the transition 48 between the distal marker band 46 and the balloon distal leg 42 enables the balloon distal leg 42 to provide the desired smaller distal profile, and enhances flexibility of the catheter 10 for the length of the balloon distal leg 42.

The marker bands 44 and 46 may of course be affixed to the inner body 26 by any suitable method, including adhesives. The illustrated embodiment shows marker bands 44 and 46 which have been swaged and compressed into the material of the inner body 26, causing a local compression of the inner body wall thickness.

The illustrated preferred embodiment of the present invention further includes an improved leading-edge distal taper 56 of the balloon distal leg 42. In prior balloon catheters, it was known to taper a leading distal edge of the balloon distal leg by grinding away some of the balloon material from the distal-most portion of the balloon distal leg in a conical shape. However, the grinding technique may produce localized heating of the balloon material due to friction, in effect a heat-treating operation, causing the tapered balloon leg portion to become stiffer. Due to mechanical limitations of the grinding equipment, the grinding technique was also incapable of producing a balloon leg leadingedge that tapers all the way to the surface of the inner body.

Accordingly, the present invention preferably provides an improved balloon distal leg leading-edge taper 56 by cutting away or shaving the balloon material in the tapering region. This shaving technique cuts away the balloon leg material without substantially heating it, and likewise without adversely affecting of the flexibility of the distal balloon leg leading-edge tapering portion. The shaving technique is also capable of producing a leading-edge tapering surface that tapers in a desired shape down to a sharp point and to the interface with the tubular inner body 26.

The present improved distal leg leading-edge taper 56 provides various benefits for an optimized balloon catheter tip design. The tapering service provides a gentle leading surface for smoothly contacting the anatomy.

The balloon catheter shown in the drawings has what is referred to as an over-the-wire configuration, in which the guidewire lumen extends throughout the length of the catheter to the proximal hub. Of course, the present invention may be used in a balloon catheter having a rapid-exchange configuration, in which the guidewire lumen extends from a distal guidewire port to a proximal port located at some intermediate position between the balloon and the proximal hub.

Various different materials may be used for the various components of a balloon catheter according to the present invention. Most of the balloon catheter components should preferably be made of materials having acceptable properties including biocompatibility, pull strength, longitudinal or column strength, and bending flexibility. Some of the preferred materials may include various plastics, referred to as polymers, including nylon, polyethylenes, polyurethanes, or PET. For example, the guidewire is preferably made of metal such as stainless steel, while the balloon 16 is preferably made of nylon. The components of the catheter shaft, including the inner and outer bodies 26 and 24, may be made of nylon, or a coextrusion of nylon and another polymer. Various radiopaque materials are available for the markers, including gold, iridium and platinum.

The present invention may of course be made with any suitable selection of dimensions and sizes. In general, the transition 48 is preferably located adjacent to or inside distal balloon leg 42. As a general example only, some possible dimensions include a first diameter 58 and first wall thickness 50 of approximately 0.020–0.040 and 0.002–0.010 respectively, all dimensions being in inches. An example of possible second diameter 60 and second wall thickness 52 of approximately 0.015–0.035 and 0.001–0.002 respectively. Likewise, the distances 66 and 68 from the distal marker band 46 to the transition 48 and to the balloon distal leg 42 may be approximately 0.10–0.25 and 0.15–0.5 respectively.

Catheter manufacturing techniques are generally known in the art, including extrusion and coextrusion, coating, adhesives, and molding. The scope of the present invention encompasses the full extent of the claims, regardless of specific materials, numbers or other details present in this description of the preferred embodiments.

One of the many possible methods of making an angioplasty balloon catheter for performing a therapeutic procedure on a patient according to the principles of the present invention includes the steps of forming a tubular inner body, a tubular outer body, and forming an angioplasty balloon using known techniques, including extrusion. The inner and outer bodies, and the balloon all define proximal and distal ends. Then, a radiopaque marker is affixed to the tubular inner body, and a mandrel is inserted within a lumen defined by the tubular inner body. A portion of the tubular inner body is drawn down distal of the radiopaque marker to a smaller wall thickness, defining a transition between the wall thicknesses. The inner body and mandrel assembly is inserted into the balloon, and the outer body is inserted within the balloon proximal leg. The balloon proximal leg is heat-sealed to the outer body, and then the distal leg of the balloon is heat sealed to the inner body at a position distal of the wall thickness transition. A distal portion of the balloon leg is then shaved to form a distal tapering portion. In addition, the shaving step may be performed before the inner body and mandrel assembly is inserted into the balloon.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A method of making an angioplasty balloon catheter for performing a therapeutic procedure on a patient, comprising the steps of:
   (a) forming a tubular inner body, a tubular outer body, and forming an angioplasty balloon; the inner and outer bodies and balloon all having proximal and distal ends;
   (b) affixing a radiopaque marker to the tubular inner body;
   (c) inserting a mandrel within a lumen defined by the tubular inner body, and drawing down a unitary portion of the tubular inner body distal of the radiopaque marker from a first wall thickness to a smaller second wall thickness, defining a transition between the first and second wall thicknesses;
   (d) inserting the inner body and mandrel assembly into the balloon;
   (e) inserting the outer body within a balloon proximal leg, and heat sealing the balloon proximal leg to the outer body; and
   (f) heat-sealing a distal leg of the balloon to the inner body at a position distal of the wall thickness transition;
   (g) shaving a distal portion of the distal balloon leg to form a distal tapering portion.

2. The method as set forth in claim 1, wherein the step (g) of shaving occurs before the step (d) of inserting the inner body and mandrel assembly into the balloon.

3. A method of making an angioplasty balloon catheter for performing a therapeutic procedure on a patient, comprising the steps of:
   (a) forming a tubular inner body, a tubular outer body, and forming an angioplasty balloon; the inner and outer bodies and balloon all having proximal and distal ends;
   (b) affixing a radiopaque marker to the tubular inner body;
   (c) inserting a mandrel within a lumen defined by the tubular inner body, and drawing down a unitary portion of the tubular inner body distal of the radiopaque marker from a first wall thickness to a smaller second wall thickness, defining a transition between the first and second wall thicknesses;
   (d) shaving a distal portion of a distal balloon leg to form a distal tapering portion;
   (e) inserting the inner body and mandrel assembly into the balloon;
   (f) inserting the outer body within a balloon proximal leg, and heat sealing the balloon proximal leg to the outer body; and
   (g) heat-sealing the distal leg of the balloon to the inner body at a position distal of the wall thickness transition.

4. A method of making an angioplasty balloon catheter for performing a therapeutic procedure on a patient, comprising the steps of:
   (a) forming a tubular inner body, a tubular outer body, and forming an angioplasty balloon; the inner and outer bodies and balloon all having proximal and distal ends;
   (b) affixing a first and second radiopaque marker to the tubular inner body;
   (c) inserting a mandrel within a lumen defined by the tubular inner body, and drawing down a unitary portion of the tubular inner body distal of the radiopaque markers from a first wall thickness to a smaller second wall thickness, defining a transition between the first and second wall thicknesses;
   (d) inserting the inner body and mandrel assembly into the balloon; and aligning each of the markers with an end of a balloon working length;
   (e) inserting the outer body within a balloon proximal leg, and heat sealing the balloon proximal leg to the outer body; and
   (f) heat-sealing a distal leg of the balloon to the inner body at a position distal of the wall thickness transition;
   (g) shaving a distal portion of the distal balloon leg to form a distal tapering portion.

* * * * *